(12) United States Patent
Peng

(10) Patent No.: US 11,583,300 B2
(45) Date of Patent: Feb. 21, 2023

(54) ULTRASONIC ROBOTIC CLEANER FREELY MOVABLE BACK AND FORTH INSIDE A BLOOD VESSEL

(71) Applicant: Zhijun Peng, Guangdong (CN)

(72) Inventor: Zhijun Peng, Guangdong (CN)

( * ) Notice: Subject to any disclaimer, the term of this patent is extended or adjusted under 35 U.S.C. 154(b) by 370 days.

(21) Appl. No.: 16/898,450

(22) Filed: Jun. 11, 2020

(65) Prior Publication Data

US 2021/0015510 A1 Jan. 21, 2021

(30) Foreign Application Priority Data

Jul. 15, 2019 (CN) .......................... 201910634331.3

(51) Int. Cl.
| | |
|---|---|
| *A61B 17/22* | (2006.01) |
| *A61B 34/30* | (2016.01) |
| *A61M 25/01* | (2006.01) |
| *A61B 1/04* | (2006.01) |
| *A61M 5/142* | (2006.01) |
| *A61M 5/30* | (2006.01) |
| *A61B 17/00* | (2006.01) |

(Continued)

(52) U.S. Cl.
CPC ........ *A61B 17/22012* (2013.01); *A61B 1/041* (2013.01); *A61B 34/30* (2016.02); *A61M 5/142* (2013.01); *A61M 5/30* (2013.01); *A61M 25/0116* (2013.01); *A61B 1/05* (2013.01); *A61B 1/0684* (2013.01); *A61B 2017/00345* (2013.01); *A61B 2017/00398* (2013.01); *A61B 2017/00734* (2013.01); *A61B 2017/22007* (2013.01); *A61B 2017/320024* (2013.01); *A61B 2034/301* (2016.02); *A61M 11/02* (2013.01)

(58) Field of Classification Search
CPC .......... A61B 2017/00345; A61B 34/32; A61B 34/72; A61B 34/73; A61B 5/6847; A61B 2560/04
See application file for complete search history.

(56) References Cited

U.S. PATENT DOCUMENTS

| | | | | |
|---|---|---|---|---|
| 2006/0257234 | A1* | 11/2006 | Park | A61B 1/041 |
| | | | | 414/730 |
| 2012/0035540 | A1* | 2/2012 | Ferren | A61B 5/076 |
| | | | | 604/95.01 |

(Continued)

FOREIGN PATENT DOCUMENTS

| | | | |
|---|---|---|---|
| CN | 101169212 A | * | 4/2008 |
| CN | 102392926 B | * | 4/2013 |

*Primary Examiner* — Tuan V Nguyen

(57) ABSTRACT

An ultrasonic robotic cleaner freely movable back and forth inside a blood vessel, having an elongated shell, electrical driving mechanisms, a storage battery, and a high frequency ultrasonic vibration unit; each electrical driving mechanism is formed by propellers, an ultra-micro motor, and a gear assembly; the high frequency ultrasonic vibration unit and the storage battery are mounted inside the elongated shell; the high frequency ultrasonic vibration unit and the ultra-micro motor are electrically connected with the storage battery; the electrical driving mechanisms are disposed at two ends of the elongated shell respectively. The robotic cleaner moves inside the blood vessel and achieves blood cavitation so that blood lipids are fragmented into finer particles which are eventually burnt due to peroxidation and metabolism and transformed into energy, water and $CO_2$.

9 Claims, 2 Drawing Sheets

(51) Int. Cl.
    *A61B 1/05*     (2006.01)
    *A61B 17/32*     (2006.01)
    *A61B 1/06*     (2006.01)
    *A61M 11/02*     (2006.01)

(56) References Cited

U.S. PATENT DOCUMENTS

2017/0119236 A1*   5/2017   Hyde .................... A61B 5/742
2018/0000502 A1*   1/2018   Baym .................... A61B 17/32

* cited by examiner

ULTRASONIC ROBOTIC CLEANER FREELY MOVABLE BACK AND FORTH INSIDE A BLOOD VESSEL

BACKGROUND OF THE INVENTION

The present invention relates to the field of cleaning apparatus that cleans intravascular blood lipids, and more specifically relates to an ultra-micro robotic cleaner that moves back and forth inside a blood vessel to clean intravascular blood lipids.

Aging and hardening of blood vessels may easily happen when we get older, and blood lipids will accumulate anywhere in blood vessels and obstruct normal blood flow. Blood vessels are clogged mainly because in certain areas of the blood vessels, vessel walls are gradually being thickened due to continuous accumulation of undesired substances on the vessel walls such as intravascular lipids and cholesterols, thereby narrowing the blood vessels and slowing down the blood flow. When blood flow slows down, lipids and cholesterols can more easily accumulate on the vessel walls. Such a vicious cycle may finally result in the blood vessels being completely clogged. In some cases, the undesired substances inside the blood vessels may fall off from the vessel walls and constitute an obstruction which are then carried by the blood flow to some other blood vessels of the body and clog the same. Especially in autumn and winter times, viscous blood may undermine blood flow; also, when weather gets drier and cooler, blood vessels may easily contract, and this is one of the reasons why cardiovascular and cerebrovascular diseases are more common during autumn and winter. Blood vessels are the passage ways that transport the blood of the entire body. If blood vessels are clogged, body health and even the life of a person may be put at grave risk.

Many methods have been used to solve the problem of clogged blood vessels, including medicinal therapy and physical cleaning therapy. Physical cleaning therapy mainly concerns development of various kinds of ultra-micro robotic devices for intravascular use. Blood vessels are cleaned and the clogging is mitigated by moving the ultra-micro robotic devices inside the blood vessels. Prior art literatures of ultra-micro robotic devices include the following:

1. CN102151162A disclosed Magnetic control blood vessel robot for cleaning thrombus. The robot consists of a miniature robot and an external driver; a liquid pump and a cylindrical pump body made by an elastic film connected inside the liquid pump in series are arranged in the miniature robot body; a plurality of permanent magnets provided with central holes are circumferentially and uniformly distributed on the outer wall of the pump body; guide rods are respectively arranged on the inner wall of a cavity of the miniature robot body at positions corresponding to the permanent magnets; each guide rod extends into the central hole of the corresponding permanent magnet; a spiral spring is sleeved on each guide rod; the external driver is provided with an annular supporting frame; and direct current electromagnets in the same quantity as the permanent magnets are uniformly distributed on the annular supporting frame. During operation, by moving the external driver, magnetic force of the external driver will drive the miniature robot inside the blood vessels to move, thereby achieving thrombus cleaning by the miniature robot inside the blood vessels.

2. CN101961261A disclosed a Jet flow-driven blood vessel robot, which consists of a capsule-shaped shell, a liquid flow control device, a wireless receiving control block and an operating device; the liquid flow control device, the wireless receiving control block and the operating device are arranged in the shell; the liquid flow control device uses blood as a medium; the liquid flow control device consists of a variable pump, 12 suction and spray nozzles and 24 two-way electromagnetic valves; the inlet and outlet of each suction and spray nozzle are connected with two pipes respectively; the two pipes are each connected with a two-position two-way electromagnetic valve in series respectively, one of the two pipes is connected with the inlet of the variable pump, and the other one of the two pipes is connected with the outlet of the variable pump; the 12 suction and spray nozzles are embedded on the wall of the shell, and their openings are configured to face outwardly from the shell. By using the variable pump, the 12 suction and spray nozzles and the 21 two-way electromagnetic valves, the blood vessel robot can move inside the blood vessel to achieve cleaning of the blood vessel.

In the above disclosed prior arts, regardless of how the robot is driven to move inside the blood vessel, a common feature in these prior art blood vessel cleaning robots is that the robot will move or flow inside the blood vessel to achieve cleaning of the blood vessel, thereby preventing clogged blood vessel. Prior art blood vessel cleaning robots cannot perform cavitation in blood vessels and fragmentation of thrombus and blood lipids, and do not have the therapeutic effect of burning intravascular lipids. Therefore, prior art blood vessel cleaning robots can only clear the blood vessels, but cannot achieve the physiotherapeutic effects of reducing blood viscosity and diluting blood. Accordingly, prior art blood vessel cleaning robots have poor therapeutic effects disadvantaged by repeated and arbitrary growth of intravascular blood lipids. In view of the above, prior art blood vessel cleaning robots are not the optimal solutions. The market desperately needs a technical solution that achieves better therapeutic effects.

BRIEF SUMMARY OF THE INVENTION

In view of the aforesaid problems and disadvantages now in the prior arts, the present invention provides an ultrasonic robotic cleaner freely movable back and forth inside a blood vessel; the robotic cleaner has an elongated shell, propeller type electrical driving mechanisms, a storage battery, and a high frequency ultrasonic vibration unit. By using the propeller type electrical driving mechanisms, the robotic cleaner is driven to move freely back and forth a blood vessel. By using the high frequency ultrasonic vibration unit, ultrasonic cavitation of blood is performed, so that cavitation and fragmentation of blood lipids are achieved such that blood lipids are fragmented into finer particles and blood molecules will move in an increased speed due to ultrasonic cavitation effect. More speedy movement of blood molecules will increase body temperature, and triglyceride being the major component in the finer particles of blood lipids will then be peroxidised and metabolized under the effect of hormones and will be eventually degraded and transformed into energy, water and $CO_2$. $CO_2$ will be breathed out of the body, while water will be discharged out of the body in the form of sweat and urine. As such, the fragmented finer lipid particles will be burnt, thereby achieving a therapeutic effect that addresses both the symptoms as well as the root cause of the symptoms. Further, as the robotic cleaner is driven to move by using the propeller type electrical driving mechanisms, thrombus relatively large in size can be dragged into the propellers where it is fragmented into finer granules able to flow in the blood, and then it is further fragmented into finer particles by ultrasonic cavitation and fragmentation. As described above the finer particles will be eventually burnt thanks to peroxidation and metabolism. Therefore, thrombus relative large in size can be destroyed.

The present invention has the following technical solutions: An ultrasonic robotic cleaner freely movable back and forth in a blood vessel, comprising an elongated shell, electrical driving mechanisms, a storage battery, and a high frequency ultrasonic vibration unit; each of the electrical driving mechanisms is formed by propellers, an ultra-micro motor, and a gear assembly; the high frequency ultrasonic vibration unit and the storage battery are mounted inside the elongated shell; the high frequency ultrasonic vibration unit and the ultra-micro motor are electrically connected with the storage battery to obtain power for operation; the high frequency ultrasonic vibration unit is a high frequency vibration motor or an ultrasonic transducer; the electrical driving mechanisms are disposed at two ends of the elongated shell respectively to drive the elongated shell to move in the blood vessel.

In order that the robotic cleaner is more stable when moving in the blood so that it will not revolve along its own axis, the gear assembly of each electrical driving mechanism is configured as a transmission mechanism that enables coaxial contra-rotation of the propellers; two propellers are mounted at an output end of the transmission mechanism; an input end of the transmission mechanism is connected with the ultra-micro motor to achieve motion transmission.

In order to reduce resistance when the robotic cleaner travels in the blood, the robotic cleaner provides some spaces for blood flow; wherein an outer surface of the elongated shell is provided with a plurality of liquid guiding grooves along a longitudinal direction of the elongated shell; the liquid guiding grooves align with and in communication with longitudinal openings on propeller shells respectively. The liquid guiding grooves allow the blood to flow through so as to reduce resistance, also, the blood flowing through the liquid guiding grooves can be subject to closer and more concentrated effect of ultrasonic cavitation, thereby obtaining better therapeutic effect.

The present invention also achieves therapeutic effect by medicinal application, wherein a liquid medicine storage chamber and electrical liquid suction pumps are disposed inside the elongated shell; each of the electrical liquid suction pumps has an input end and an output end; the input end of each electrical liquid suction pump is connected with the liquid medicine storage chamber to achieve suction of liquid medicine from the liquid medicine storage chamber; the output end of each electrical liquid suction pump is connected with a corresponding nozzle provided on the elongated shell to spray the liquid medicine out of the elongated shell.

In order to recharge the robotic cleaner externally outside of the robotic cleaner, so that it can operate to move back and forth inside the blood vessel for a long period of time, a wireless charging module is provided on an inner side wall of the elongated shell; the wireless charging module comprises a wireless charging coil and a wireless charging circuit; the wireless charging module is electrically connected with the storage battery.

In order to facilitate doctors to retrieve intravascular images and videos, the elongated shell or each of the propeller shells is provided with a pinhole camera and an LED.

The present invention has the following beneficial advantages: The present invention has an elongated shell, propeller type electrical driving mechanisms, a storage battery, and a high frequency ultrasonic vibration unit. By using the propeller type electrical driving mechanisms, the robotic cleaner is driven to move freely back and forth a blood vessel. By using the high frequency ultrasonic vibration unit, ultrasonic cavitation of blood is performed, so that cavitation and fragmentation of blood lipids are achieved such that blood lipids are fragmented into finer particles and blood molecules will move in an increased speed due to ultrasonic cavitation effect. More speedy movement of blood molecules will increase body temperature, and triglyceride being the major component in the finer particles of blood lipids will then be peroxidised and metabolized under the effect of hormones and will be eventually degraded and transformed into energy, water and $CO_2$. $CO_2$ will be breathed out of the body, while water will be discharged out of the body in form of sweat and urine. As such, the fragmented finer lipid particles will be burnt, thereby achieving a therapeutic effect that addresses both the symptoms as well as the root cause of the symptoms. Further, as the robotic cleaner is driven to move by using the propeller type electrical driving mechanisms, thrombus relatively large in size can be dragged into the propellers where it is fragmented into finer granules able to flow in the blood, and then it is further fragmented into finer particles by ultrasonic cavitation and fragmentation. As described above the finer particles will be eventually burnt thanks to peroxidation and metabolism. Therefore, thrombus relative large in size can be destroyed. The present invention is scientifically based and achieves a therapeutic effect that addresses both the symptoms as well as the root cause of the symptoms. Also, the present invention has a simple structure.

DETAILED DESCRIPTION OF THE INVENTION

Figure 1:
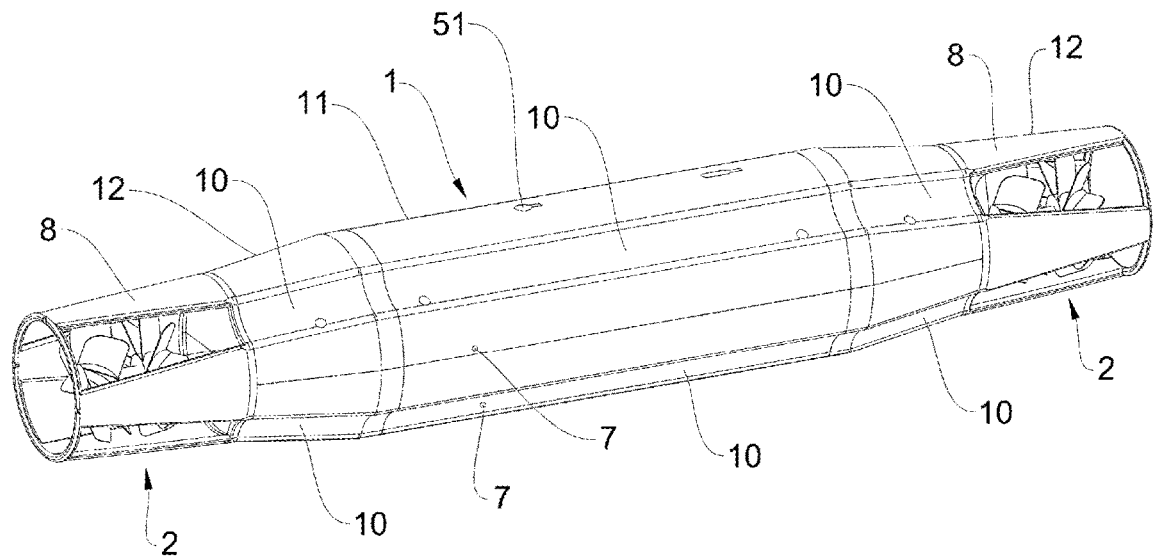
FIG. 1 is a perspective structural view of the present invention.
Figure 2:
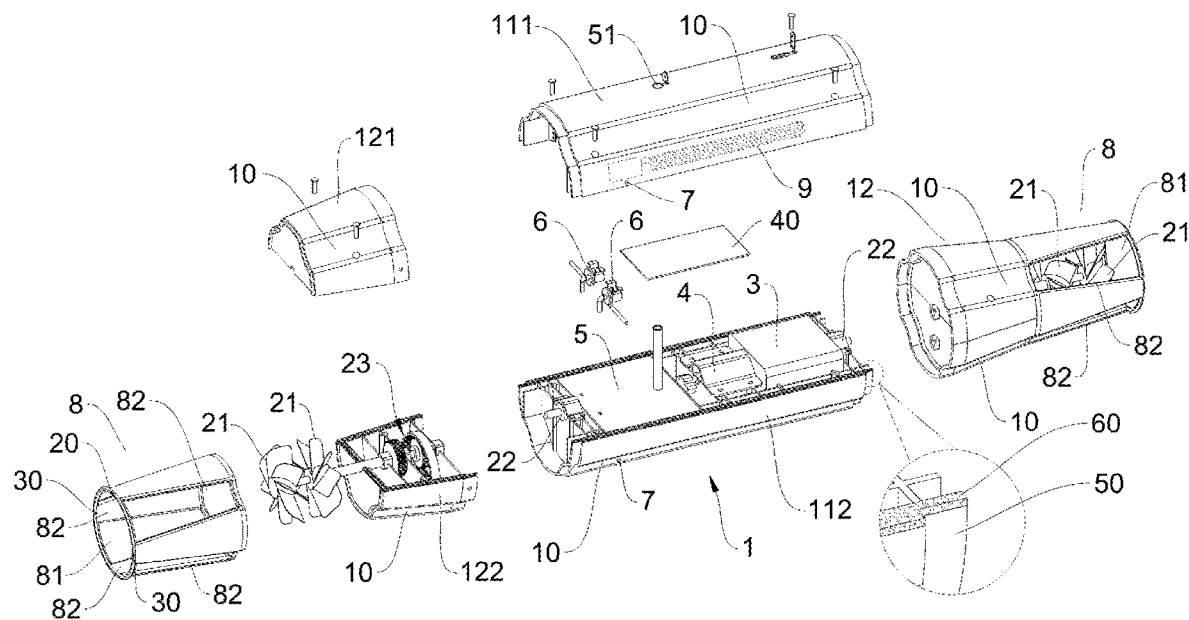
FIG. 2 is an exploded structural view of the present invention.
Figure 3:
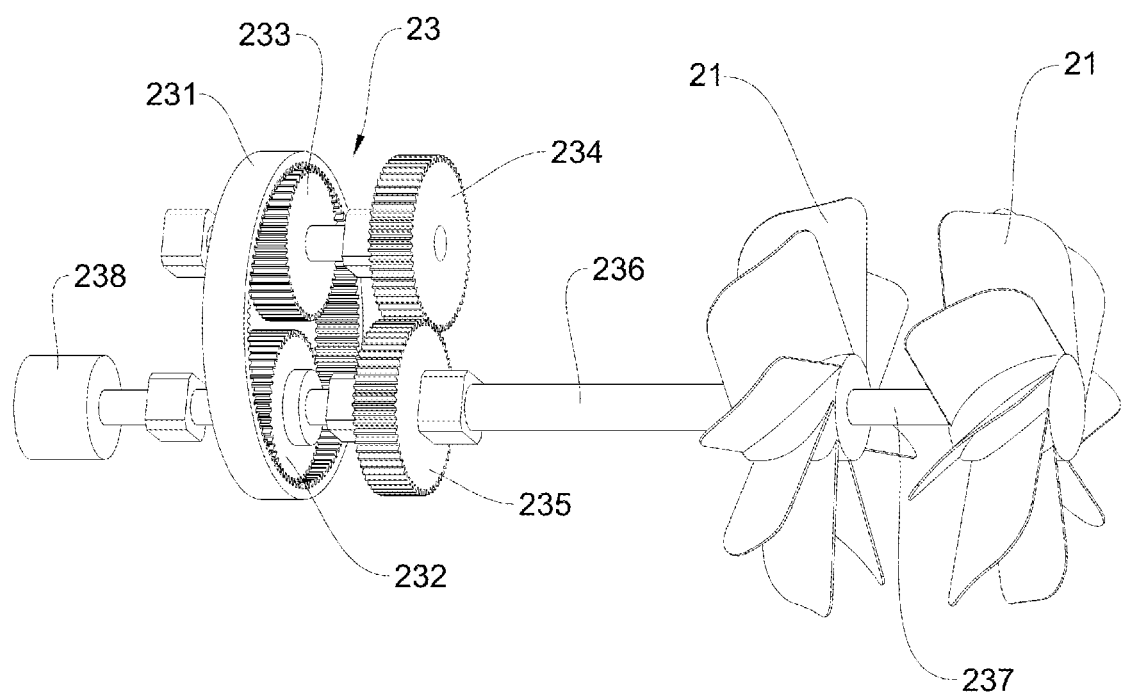
FIG. 3 is a perspective structural view showing the propellers and a transmission mechanism that enables coaxial contra-rotation of the propellers according to the present invention.

As shown in FIGS. 1-3, the present invention is an ultrasonic robotic cleaner freely movable back and forth in a blood vessel, comprising major components such as an elongated shell 1, electrical driving mechanisms 2, a storage battery 3, a high frequency ultrasonic vibration unit 4, and a central control circuit board 40.

As shown in FIGS. 2 and 3, each of the electrical driving mechanisms 2 is formed by propellers 21, an ultra-micro motor 22, and a gear assembly 23. Also, in order that the robotic cleaner is more stable when moving in the blood so that it will not revolve along its own axis, the gear assembly 23 of each electrical driving mechanism 2 is configured as a transmission mechanism that enables coaxial contra-rotation of the propellers. Specifically, two propellers 21 are mounted at an output end of the transmission mechanism. An input end of the transmission mechanism is connected with the ultra-micro motor 22 to achieve motion transmission. The transmission mechanism is the mechanism driving propellers, as commonly used in torpedo. The transmission mechanism can drive one of the propellers 21 to rotate clockwise while driving another one of the propellers 21 to rotate anti-clockwise, and this can stabilize, balance, and move the robotic cleaner along a determined direction without causing the robotic cleaner to revolve around its own axis when the robotic cleaner is driven to move through the blood vessel. The transmission mechanism can have several different specific structural configurations. In the embodiment disclosed herein in FIG. 3, the transmission mechanism mainly comprises an outer teethed belt 231, a first gear 232, a second gear 233, a third gear 234, a fourth gear 235, an inner transmission shaft 236 and an outer transmission shaft 237 sleeved inside the inner transmission shaft 236, and an input end 238 connected with the ultra-micro motor 22. One of the propellers 21 is connected with the inner transmission shaft 236; another one of the propellers 21 is connected with the outer transmission shaft 237. A person skilled in the art can search on the internet (e.g. "Baidu" search engine) for more possible structural configurations of the transmission mechanism that achieves coaxial contra-rotation of propellers. The transmission mechanism that achieves coaxial contra-rotation of propellers will not be described in detail herein.

As shown in FIG. 2, the high frequency ultrasonic vibration unit 4 and the storage battery 3 are mounted inside the elongated shell 1. The high frequency ultrasonic vibration unit 4 and the ultra-micro motor 22 are electrically connected with the storage battery 3 to obtain power for operation. The high frequency ultrasonic vibration unit 4, the ultra-micro motor 22 and the storage battery 3 are electrically connected with the central control circuit board 40 in order to be operated under the control of programs configured in the central control circuit board 40. The high frequency ultrasonic vibration unit 4 is a high frequency vibration motor or an ultrasonic transducer. When an ultrasonic transducer is used, a driving circuit or an ultrasonic generation circuit that drives and controls operation of the ultrasonic transducer should be configured within the central control circuit board 40. The storage battery 3 is a graphene battery of ultra-high density and ultra-small size.

As shown in FIG. 1, the electrical driving mechanisms 2 are disposed at two ends of the elongated shell 1 respectively to drive the elongated shell 1 to move in blood. In order to obtain a stronger driving power and allow the robotic cleaner to move back and forth freely inside the blood vessel, as shown in the exemplary embodiment illustrated in FIG. 1, two electrical driving mechanisms 2 are provided, each disposed at a respective end of the elongated shell 1.

To prevent the blades of the propellers from injuring the vessel wall when the robotic cleaner moves inside the blood vessel, FIGS. 1-2 show that propeller shells 8 are provided at two ends of the elongated shell 1. Each of the propeller shells 8 is configured with a front end opening 81 and a plurality of longitudinal openings 82 around an outer surface of the propeller shell 8. The propellers 21 are disposed in each propeller shell 8. Likewise, when two ends of the elongated shell 1 are each provided with a corresponding electrical driving mechanism 2, two ends of the elongated shell 1 are also each provided with a corresponding propeller shell 8 corresponding to the electrical driving mechanism. In other words, inside each propeller shell 8, two coaxial contra-rotating propellers 21 driven by a corresponding transmission mechanism are provided.

In order to reduce resistance when the robotic cleaner travels in the blood, the robotic cleaner provides some spaces for blood flow. As shown in FIG. 1 or FIG. 2, an outer surface of the elongated shell 1 is provided with a plurality of liquid guiding grooves 10 along a longitudinal direction of the elongated shell 1. The liquid guiding grooves 10 align with and in communication with the longitudinal openings 82 on the propeller shells 8 respectively. The liquid guiding grooves 10 allow the blood to flow through so as to reduce resistance, also, the blood flowing through the liquid guiding grooves 10 can be subject to closer and more concentrated effect of ultrasonic cavitation, thereby obtaining better therapeutic effect. Specifically, when the blood is driven by the propellers out of the longitudinal openings 82 and flows through the liquid guiding grooves 10, a physical distance between the blood and the high frequency ultrasonic vibration unit 4 is the smallest when blood flowing through the liquid guiding grooves 10 passes by the high frequency ultrasonic vibration unit 4, and at this smallest physical distance, high frequency ultrasonic cavitation of the high frequency ultrasonic vibration unit 4 is the strongest. Therefore, movement of blood molecules will be accelerated, and body temperature will rise more rapidly, thereby burning more lipid particles and thus achieving greater therapeutic efficiency.

In order to further equip the present invention with more functions so as to further enhance the therapeutic effect of the present invention, FIG. 2 shows that the present invention also achieves therapeutic effect by medicinal application. Specifically, a liquid medicine storage chamber 5 and electrical liquid suction pumps 6 are disposed inside the elongated shell 1. Each of the electrical liquid suction pumps 6 has an input end and an output end. The input end of each electrical liquid suction pump 6 is connected with the liquid medicine storage chamber 5 to achieve suction of liquid medicine from the liquid medicine storage chamber 5 The output end of each electrical liquid suction pump 6 is connected with a corresponding nozzle 7 provided on the elongated shell 1 to spray the liquid medicine out of the elongated shell 1. The electrical suction pumps 6 are electrically connected with the central control circuit board 40 so as to obtain electrical operating signals from the central control circuit board 40. Further, in order that the liquid medicine can be replenished to sustain the function of spraying liquid medicine, FIG. 1 or 2 illustrates a liquid medicine replenishment opening 51 coverable by a cap; the liquid medicine replenishment opening 51 is in communication with the liquid medicine storage chamber 5.

In order to recharge the robotic cleaner externally outside of the robotic cleaner, so that it can operate to move back and forth inside the blood vessel for a long period of time, FIG. 2 illustrates a wireless charging module 9 on an inner side wall of the elongated shell 1. The wireless charging module 9 comprises a wireless charging coil and a wireless charging circuit. The wireless charging module 9 is electrically connected with the storage battery 3. When the present invention is sold by retailers, the present invention is also sold together with a wireless charging seat module cooperative with the wireless charging module 9. When users place the wireless charging seat module on the skin, the robotic cleaner can be wirelessly charged.

In order to facilitate doctors to retrieve intravascular images and videos, the elongated shell 1 or each of the propeller shells 8 is provided with a pinhole camera 20 and an LED 30. The pinhole camera 20 and the LED 30 are electrically connected with the central control circuit board 40. An ultra-micro wireless communication (BLUETOOTH®) module is also correspondingly provided on the central control circuit board 40, so that the images and videos being captured and filmed can be shared to and used by external devices.

To further optimize the structural configuration of the present invention, so that is can be more easily produced and processed, FIG. 2 shows that the elongated shell 1 comprises a primary shell 11 and secondary shells 12 at two ends of the primary shell 11 respectively, wherein the primary shell 11 is formed by an upper shell 111 and a lower shell 112 connected to each other. A mounting cavity is formed between a space enclosed by the upper shell 111 and the lower shell 112. The ultra-micro motor 22, the liquid medicine storage chamber 5, the electrical suction pumps 6, the storage battery 3 and the high frequency ultrasonic vibration unit 4 are disposed in the mounting cavity of the primary shell 11. Each of the secondary shells 12 is formed by an upper secondary shell 121 and a lower secondary shell 122; a mounting cavity is also formed between a space enclosed by the upper secondary shell 121 and the lower secondary shell 122. The corresponding gear assembly 23 is mounted inside the mounting cavity of the secondary shell 12. Connecting portions 60 between the primary shell 11 and each of the secondary shells 12 are each provided with a sealing ring 50 to ensure air tightness. As shown in FIG. 2, the ultra-micro motor 22 is connected to a corresponding gear assembly 23 inside a corresponding secondary shell 12 via a transmission shaft; the propeller shells 8 are provided at end surfaces of the secondary shells 12 respectively. The wireless charging module 9 is disposed on an inner surface of either the upper shell 111 or the lower shell 112.

The present invention is substantially operated as follows: Besides the robotic cleaner described above, a robotic cleaner operating device, or a central computer, or a smart portable phone, or a tablet computer which can control operation of the robotic cleaner wirelessly is generally required. The robotic cleaner operating device, the central computer, the smart portable phone or the tablet computer as mentioned is considered a robotic cleaner operating platform. The robotic cleaner operating platform establishes communication with the robotic cleaner via wireless communication to control the robotic cleaner to move. During use, prior art medical technologies such as CT equipment, X-ray equipment and contrast agents are employed for angiography to reveal images of the blood vessels of the entire human body. By checking the obtained images of blood vessels, clogged blood vessel can be identified. By means of minimally invasive surgery at the spot where the clogged blood vessel is identified, the robotic cleaner of the present invention is placed inside the clogged blood vessel, and the doctor can control the robotic cleaner remotely and wirelessly through the robotic cleaner operating platform, such that the robotic cleaner can be moved and positioned at the clogged position of the blood vessel, and next, the ultrasonic function of the present invention will be activated to perform cavitation to clean the thrombus and blood lipids in the blood ultrasonically, thereby achieving the object of body health maintenance. Further, the doctor may move the robotic cleaner to a section of the blood vessel through the robotic cleaner operating platform and move the robotic cleaner to perform ultrasonic cavitation back and forth within said section of the blood vessel.

What is claimed is:

1. An ultrasonic robotic cleaner, comprising an elongated shell, electrical driving mechanisms, a storage battery, and a high frequency ultrasonic vibration unit;
    each of the electrical driving mechanisms is formed by propellers, an ultra-micro motor, and a gear assembly;
    the high frequency ultrasonic vibration unit and the storage battery are mounted inside the elongated shell; the high frequency ultrasonic vibration unit and the ultra-micro motor are electrically connected with the storage battery to obtain power for operation;
    the high frequency ultrasonic vibration unit is a high frequency vibration motor or an ultrasonic transducer;
    the electrical driving mechanisms are disposed at two ends of the elongated shell respectively to drive the elongated shell to move.

2. The ultrasonic robotic cleaner of claim 1, wherein the gear assembly of each electrical driving mechanism is configured as a transmission mechanism that enables coaxial contra-rotation of the propellers; two propellers are mounted at an output end of the transmission mechanism; an input end of the transmission mechanism is connected with the ultra-micro motor to achieve motion transmission.

3. The ultrasonic robotic cleaner of claim 2, wherein propeller shells are provided at two ends of the elongated shell respectively; each of the propeller shells is configured with a front end opening and a plurality of longitudinal openings around an outer surface of the propeller shell; the propellers are disposed in each propeller shell.

4. The ultrasonic robotic cleaner of claim 3, wherein an outer surface of the elongated shell is provided with a plurality of liquid guiding grooves along a longitudinal direction of the elongated shell; the liquid guiding grooves align with and in communication with the longitudinal openings on the propeller shells respectively.

5. The ultrasonic robotic cleaner of claim 1, wherein a liquid medicine storage chamber and electrical liquid suction pumps are disposed inside the elongated shell; each of the electrical liquid suction pumps has an input end and an output end; the input end of each electrical liquid suction pump is connected with the liquid medicine storage chamber to achieve suction of liquid medicine from the liquid medicine storage chamber; the output end of each electrical liquid suction pump is connected with a corresponding nozzle provided on the elongated shell to spray the liquid medicine out of the elongated shell.

6. The ultrasonic robotic cleaner of claim 5, wherein a liquid medicine replenishment opening coverable by a cap is provided on the elongated shell; the liquid medicine replenishment opening is in communication with the liquid medicine storage chamber.

7. The ultrasonic robotic cleaner of claim 3, wherein a wireless charging module is provided on an inner side wall of the elongated shell; the wireless charging module comprises a wireless charging coil and a wireless charging circuit; the wireless charging module is electrically connected with the storage battery.

8. The ultrasonic robotic cleaner of claim 3, wherein the elongated shell or each of the propeller shells is provided with a pinhole camera and a light emitting diode (LED).

9. The ultrasonic robotic cleaner of claim 7, wherein the elongated shell comprises a primary shell and secondary shells at two ends of the primary shell respectively,
    wherein the primary shell is formed by an upper shell and a lower shell connected to each other; a mounting cavity is formed between a space enclosed by the upper shell and the lower shell; the ultra-micro motors, the liquid medicine storage chamber, the electrical suction pumps, the storage battery and the high frequency ultrasonic vibration unit are disposed in the mounting cavity of the primary shell;
    each of the secondary shells is formed by an upper secondary shell and a lower secondary shell; a mounting cavity is also formed between a space enclosed by the upper secondary shell and the lower secondary shell; the corresponding gear assembly is mounted inside the mounting cavity of the secondary shell;

each of the ultra-micro motors is connected to the corresponding gear assembly inside each corresponding secondary shell via a transmission shaft;

the propeller shells are provided at end surfaces of the secondary shells respectively;

the wireless charging module is disposed on an inner surface of either the upper shell or the lower shell.

* * * * *